(12) United States Patent
Schaedlich et al.

(10) Patent No.: US 7,799,113 B2
(45) Date of Patent: *Sep. 21, 2010

(54) CONDITIONING SYSTEM AND METHOD FOR USE IN THE MEASUREMENT OF MERCURY IN GASEOUS EMISSIONS

(75) Inventors: Frank H. Schaedlich, Toronto (CA); Daniel R. Schneeberger, Scarborough (CA); Glenn A. Norton, Ames, IA (US)

(73) Assignee: Tekran Instruments Corporation (CA)

( * ) Notice: Subject to any disclaimer, the term of this patent is extended or adjusted under 35 U.S.C. 154(b) by 620 days.

This patent is subject to a terminal disclaimer.

(21) Appl. No.: 11/086,480

(22) Filed: Mar. 22, 2005

(65) Prior Publication Data

US 2006/0042418 A1 Mar. 2, 2006

Related U.S. Application Data

(63) Continuation-in-part of application No. 10/931,987, filed on Sep. 2, 2004, now Pat. No. 7,618,581.

(51) Int. Cl.
*C22B 43/00* (2006.01)
*A62D 3/40* (2007.01)

(52) U.S. Cl. .......................... 75/670; 588/312; 588/321
(58) Field of Classification Search .................. 75/670; 588/312, 321

See application file for complete search history.

(56) References Cited

U.S. PATENT DOCUMENTS 3,713,776 A 1/1973 Capuano
3,813,330 A 5/1974 Givens et al.

(Continued)

FOREIGN PATENT DOCUMENTS

CA 2480531 A1 3/2005

(Continued)

OTHER PUBLICATIONS

"quartz." Lewis, Richard J., Sr. (2002). Hawley's Condensed Chemical Dictionary (14th Edition). John Wiley & Sons. <http://knovel.com/web/portal/browse/display?_EXT_KNOVEL_DISPLAY_bookid=704&VerticalID=0>.*

(Continued)

*Primary Examiner*—Roy King
*Assistant Examiner*—Tima M McGuthry-Banks
(74) *Attorney, Agent, or Firm*—Paul & Paul

(57) ABSTRACT

Embodiments of the invention relate generally to systems used to measure mercury in gaseous emissions. In one aspect, the invention is directed to the use of an inert covalently bonded material selected from silicon carbide (SiC), silicon oxides ($SiO_n$, n=1-2), silicon nitride (e.g. $Si_3N_4$), silicon boride (e.g. $SiB_6$), boron nitride (e.g. BN) and mixtures thereof as material for a thermal pyrolysis unit. In another aspect, the invention is directed to an improved pyrolyzer design, in which a thermal pyrolysis unit comprises a tailpiece that allows water to be injected at the heated exit of the thermal pyrolysis unit. In another aspect, the invention is directed to the use of a coalescing filter in a scrubbing unit. In another aspect, the invention is directed to the use of a hydrophobic filter element in a scrubbing unit. One or more of these elements may be used in a conditioning module of a continuous emissions monitoring system, for example.

14 Claims, 6 Drawing Sheets

U.S. PATENT DOCUMENTS

| | | | |
|---|---|---|---|
| 3,933,431 A | | 1/1976 | Trujillo et al. |
| 4,161,883 A | | 7/1979 | Laird et al. |
| 4,379,412 A | | 4/1983 | Wood |
| 4,484,481 A | | 11/1984 | Laird et al. |
| 5,237,881 A | | 8/1993 | Ross |
| 5,277,056 A | | 1/1994 | Braun et al. |
| 5,361,514 A | * | 11/1994 | Lahoda et al. ............... 34/391 |
| 5,362,468 A | * | 11/1994 | Coulon et al. ........... 423/445 R |
| 5,458,010 A | | 10/1995 | Traina et al. |
| 5,597,535 A | | 1/1997 | Schaedlich et al. |
| 5,660,795 A | | 8/1997 | Schaedlich et al. |
| 5,750,992 A | | 5/1998 | Van Pelt et al. |
| 5,808,178 A | | 9/1998 | Rounbehler et al. |
| 5,879,948 A | | 3/1999 | Van Pelt et al. |
| 6,326,326 B1 | | 12/2001 | Feng et al. |
| 6,475,802 B2 | * | 11/2002 | Schaedlich et al. ............ 436/81 |
| 6,487,920 B1 | | 12/2002 | Robbat, Jr. |
| 6,520,033 B1 | | 2/2003 | Schroeder et al. |
| 6,558,626 B1 | | 5/2003 | Aker et al. |
| 6,627,454 B2 | | 9/2003 | Amirav et al. |
| 6,736,883 B2 | | 5/2004 | Sjostrom et al. |
| 7,618,581 B2 | * | 11/2009 | Schaedlich et al. .......... 266/148 |
| 2001/0041151 A1 | | 11/2001 | Gorecki et al. |
| 2002/0020209 A1 | | 2/2002 | Grob et al. |
| 2002/0068024 A1 | | 6/2002 | Park et al. |
| 2003/0051662 A1 | | 3/2003 | Lee et al. |
| 2003/0110950 A1 | | 6/2003 | Sjostrom et al. |
| 2004/0038414 A1 | | 2/2004 | Winkler et al. |
| 2004/0044110 A1 | * | 3/2004 | Baay et al. ................... 524/430 |
| 2005/0061110 A1 | * | 3/2005 | Schaedlich et al. ............ 75/670 |
| 2006/0042418 A1 | | 3/2006 | Schaedlich et al. |

FOREIGN PATENT DOCUMENTS

| | | |
|---|---|---|
| WO | WO 9725612 | 7/1997 |
| WO | 0223182 A1 | 3/2002 |

OTHER PUBLICATIONS

"cristobalite." Dictionary.com Unabridged (v 1.1). Random House, Inc. Mar. 25, 2009. <Dictionary.com http://dictionary.reference.com/browse/cristobalite>.*

Zamzow, Daniel S. et al., "Real-Time Atomic Absorption Mercury Continuous Emission Monitor", (2003) Review of Scientific Instruments vol. 74, No. 8, pp. 3774-3783.

* cited by examiner

CONDITIONING SYSTEM AND METHOD FOR USE IN THE MEASUREMENT OF MERCURY IN GASEOUS EMISSIONS

CROSS-REFERENCE TO RELATED APPLICATION

This is a continuation-in-part application of U.S. application Ser. No. 10/931,987 now U.S. Pat. No. 7,618,581 filed Sep. 2, 2004.

FIELD OF THE INVENTION

The present invention relates generally to mercury detection systems, and more particularly to conditioning systems and methods that may be employed in the measurement of gaseous mercury in combustion and process gas emissions.

BACKGROUND OF THE INVENTION

Governments, power utilities and researchers have recognized the need for a viable system to continuously detect and monitor mercury emissions in stack emissions and process gases. A number of proposed solutions exist in the prior art.

For example, some known conventional direct wet chemical analyzers use wet chemical reagents to condition gas samples for subsequent analysis by atomic absorption (AA) detectors, for example. Stannous chloride, sodium borohydride, or other chemical reductants may be used to convert the different mercury species to elemental form. However, these analyzers may suffer problems with sensitivity since the AA detectors generally have detection limits in the 1 $\mu g/m^3$ range and cannot quantitate values of less than several $\mu g/m^3$. While these analyzers may be useful in monitoring the emissions of waste incinerators for example, they are less useful in monitoring mercury in power plant emissions where greater sensitivity is required.

Another known wet chemical system uses a wet chemical front end, followed by gold preconcentration and detection using atomic fluorescence. The system samples full strength stack gas and splits the sample into a first path that uses an alkaline-based stannous chloride solution to convert all mercury forms into elemental mercury, and a second path that uses a tris-buffer or potassium chloride (KCl) solution to scrub out ionic mercury while passing elemental mercury. This system, however, requires the complex preparation of two different, low mercury reagents on a continuing basis, and is subject to high maintenance when used for extended periods of time. Use of liquid chemical agents may also produce toxic waste.

As a further example, conventional thermal conversion analyzers use thermal pyrolysis units to decompose the ionic mercury in gas samples into elemental form for subsequent analysis by AA detectors, for example, to determine a measure of the total mercury in the samples. Some known analyzers of this type utilize a stainless steel thermal pyrolysis unit coupled to a gold adsorption cartridge; mercury is adsorbed onto the cartridge during sampling and is thermally desorbed during an analysis phase. However, these analyzers typically suffer from recombination problems in the presence of hydrogen chloride (HCl) or chlorine ($Cl_2$). In particular, the very poor transport characteristics of mercury chloride ($HgCl_2$) means that this component of sample gas will not reach the gold cartridge in a timely manner, resulting in erroneous readings and memory effects. Even where direct AA analyzers are used, $HgCl_2$ may not be detected at all within the AA cell since it does not absorb efficiently at the primary mercury adsorption line.

Some other known thermal conversion analyzers utilize carbon-based pyrolysis units. The problem with these pyrolysis units is that impure substances that prevent the reduction of the mercury or its release from the carbon, or which reoxidize already-reduced mercury, may accumulate in the carbon. In fact, conventional materials such as carbon, as well as quartz chips, stainless steel, alumina, and molecular sieve materials may produce excessive recombination after a period of continuous running, even where the concentration of stack gas components may have been greatly reduced through prior dilution.

Some attempts have been made to utilize solid sorbents such as calcium carbonate, sodalime, and calcium oxide to remove acid gases. However, these have not been applied commercially to a large extent, due to their very short lifetimes and their tendency to affect the accuracy of mercury readings towards the end of their lifetimes. The characteristics of solid sorbents may also change whenever the sample matrix changes.

The reliability of some other proposed remedies in preventing the formation of oxidized forms of mercury, such as the injection of hydrogen gas into a stack matrix after thermal dissociation, may also be questionable. The injection of hydrogen favors the creation of HCl, which is a powerful compound for causing recombination of elemental mercury into molecular species.

SUMMARY OF THE INVENTION

Embodiments of the invention relate generally to improved systems and methods for detecting total mercury and/or speciating mercury. In at least one embodiment of the invention, an improved conditioning module is provided, which may be used in a continuous emissions monitoring system (CEM) to analyze stack gas emissions, for example.

In one broad aspect, the invention is generally directed to the use of silicon carbide as pyrolyzer material in a thermal pyrolysis unit. In another broad aspect, the invention is directed to the use of an inert covalently bonded material selected from silicon carbide (SiC), silicon oxides ($SiO_n$, n=1-2), silicon nitride (e.g. $Si_3N_4$), silicon boride (e.g. $SiB_6$), boron nitride (e.g. BN) and mixtures thereof as pyrolyzer material in a thermal pyrolysis unit. The inventors have realized that these materials provide the ability to reduce all forms of mercury to elemental form, and further, prevent recombination before the removal of acid gas species. These materials are unusually resilient, for thermal pyrolyzers operating over a wide temperature range and with a wide variety of gas matrices.

BRIEF DESCRIPTION OF THE DRAWINGS

For a better understanding of various embodiments of the invention, reference will now be made, by way of example, to the accompanying drawings in which.

DETAILED DESCRIPTION OF EMBODIMENTS OF THE INVENTION

At least some embodiments of the invention relate generally to a system for monitoring mercury in gaseous emissions, comprising: a sampling probe for sampling the emissions; a conditioning module coupled to the sampling probe, which may be adapted to speciate mercury in the emissions, the conditioning module adapted for coupling to a mercury analyzer; a calibration module coupled to the sampling probe; and a controller coupled to the conditioning module and the calibration module. The conditioning module comprises a thermal converter and, in some embodiments, one or more scrubbing units. The thermal converter comprises one or more pyrolyzer units, wherein at least one of the pyrolyzer units comprises material composed of an inert covalently bonded material selected from silicon carbide (SiC), silicon oxides ($SiO_n$, n=1-2), silicon nitride (e.g. $Si_3N_4$), silicon boride (e.g. $SiB_6$), boron nitride (e.g. BN) and mixtures thereof. At least one of the scrubbing units may comprise a coalescing filter used as an interference scrubber and gas/liquid separator. At least one of the scrubbing units may comprise a hydrophobic filter membrane. These and other features of various embodiments of the invention will now be described in greater detail with reference to the Figures.

Figure 1:
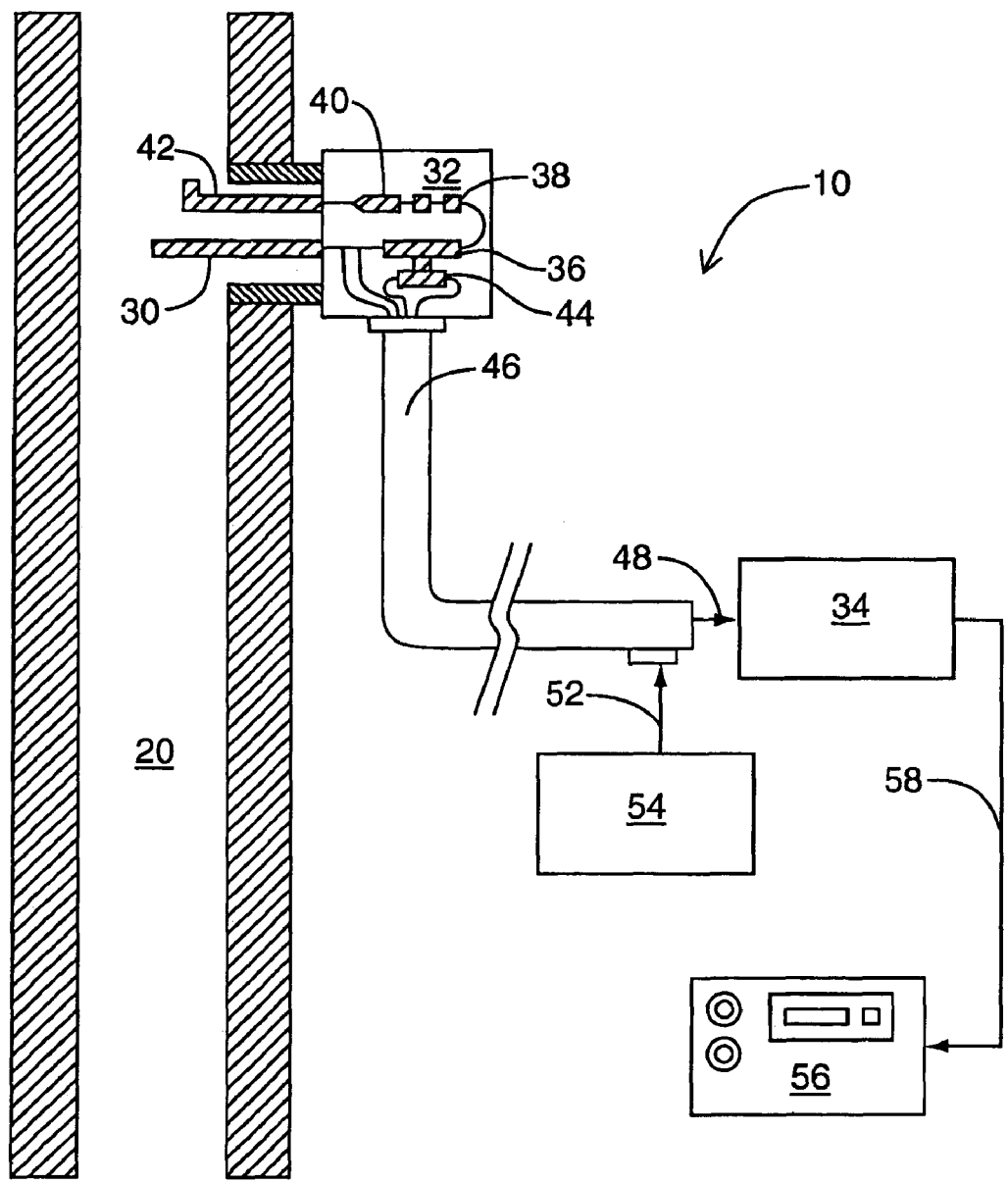
FIG. 1 is a schematic diagram illustrating components of an example implementation of a continuous emissions monitoring system (CEM)

Referring to FIG. 1, a schematic diagram illustrating components of an example implementation of a continuous emissions monitoring system (CEM) is shown generally as 10. CEM 10 is used to monitor stack gases, and a typical industrial stack is shown schematically at 20. Stack 20 may produce gaseous emissions generated from coal-fired power plants, for example. It will be understood by persons skilled in the art that in some implementations, CEM 10 may be used in the analysis of emissions from other industrial sources (e.g. waste incinerators or industrial process gases) and in applications such as speciation studies, bench scale testing, mercury removal process monitoring, and other analyses.

In this example implementation of CEM 10, a sample of stack gas is drawn off from stack 20 by a heated probe element 30 coupled to a sampling probe 32 mounted to stack 20. Sampling probe 32 is used to retrieve and preprocess the sample before it is sent to a conditioning module 34 for subsequent processing. In one example implementation, sampling probe 32 is a conventional high flow rate inertial probe used to minimize mercury measurement artifacts due to filtering. The sample retrieved by probe element 30 is passed through a coated inertial filter 36 of sampling probe 32, which is then passed through a flow sensor 38 by a pump 40 back out to stack 20 via probe element 42. During this process, a subsample is retrieved through inertial filter 36 to be diluted using a diluter 44, which is then transferred at a high velocity through a heated sample line 46 to conditioning module 34 at 48. Dilution at the sampling point enables CEM 10 to respond rapidly to changes in mercury concentrations in gas samples, since it reduces the concentration of mercury and stack gas components within the transfer line and conditioning module components.

The transfer temperature is chosen to allow rapid quantitative transport of the mercury species through heated sample line 46 without materially affecting the speciation. Temperatures of about 100 to about 180° C. can typically be used for heated sample line 46. Heated sample line 46 may also be used to send zero or dilution air [not shown] provided by conditioning module 34 to sampling probe 32. Heated sample line 46 may also be used to send data signals and the main flow eductor supply air (i.e. motive air supply) [not shown] to sampling probe 32. Heated sample line 46 may also be used to send spike and calibration gases provided through outlets 52 of a calibration module 54 to sampling probe 32 for calibration purposes. Calibration module 54 provides a source of constant, known concentration elemental mercury to CEM 10 for calibration and sample spiking purposes.

CEM 10 also comprises a mercury analyzer 56 to analyze output from conditioning module 34 at 58. In one example implementation, mercury analyzer 56 is a conventional gold pre-concentration/atomic fluorescence analyzer of the type described in U.S. Pat. No. 5,597,535, the contents of which are herein incorporated by reference. Other U.S. patents issued to the present inventors and related generally to mercury detection are U.S. Pat. Nos. 5,660,795 and 6,475,802, the contents of which are herein incorporated by reference.

A computerized control system [not shown] controls each module and the sampling probe within CEM 10. All temperatures, flows and pressures are displayed by an application program, and may be set by authorized users. The control system may feature remote operation and problem diagnosis, either via a modem and telephone line or through the Internet.

Embodiments of the invention relate generally to an improved conditioning module that may be used in a CEM (e.g. conditioning module 34 of CEM 10 of FIG. 1). It will be understood by persons skilled in the art that CEM 10 of FIG. 1 is illustrative of only one example implementation. A conditioning module constructed in accordance with an embodiment of the invention may be used in CEMs of different configurations and constructions in variant implementations. In particular, a conditioning module constructed in accordance with an embodiment of the invention may be used with other probes (e.g., most conventional probes capable of quantitatively sampling mercury species while excluding particulates, inertial probes, extraction probes), other calibration modules, other sample line configurations and constructions, other mercury analyzers (e.g., atomic fluorescence analyzers, atomic absorption analyzers), and other control systems, for example, in variant implementations of a CEM. By way of further example, the various modules could also be combined into one physical unit, eliminating the heated line, in variant implementations.

A conditioning module constructed in accordance with an embodiment of the invention will now be described in greater detail with reference to FIG. 2.

Figure 2:
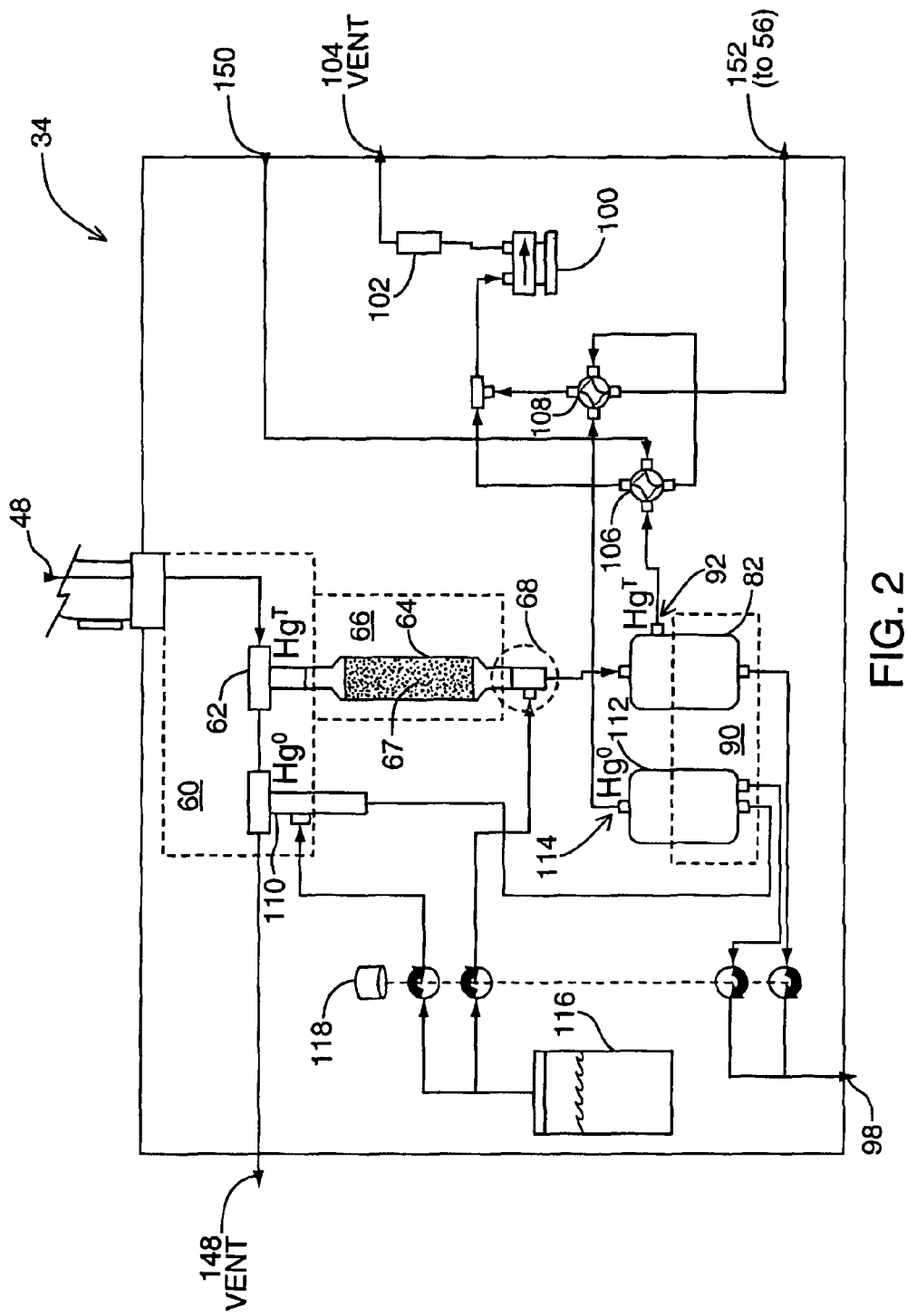
FIG. 2 is a schematic diagram of a conditioning module in an embodiment of the invention.

Referring now to FIG. 2, a schematic diagram of a conditioning module in an embodiment of the invention is shown generally as 34. Conditioning module 34 may be used in a CEM, such as the implementation of CEM 10 shown in FIG. 1, for example.

Conditioning module 34 (which may also be referred to more generally as a conditioning system) is adapted to provide either or both total mercury or elemental mercury values. Conditioning module 34 speciates mercury in a gas sample provided as input at 48 into elemental and ionic (water-soluble) forms without the use of chemical reagents or solid sorbents. This is performed through thermal pyrolysis and, optionally, pre-dilution of the gas sample, in order to eliminate recombination of pyrolyzed mercury into molecular form.

A gas sample is received by conditioning module 34 as input at 48 (e.g. as obtained from sampling probe 32 of FIG.

1), and enters a heated enclosure 60 in conditioning module 34. The gas sample is split into two streams, each corresponding to a different analytical path.

First Analytical Path: Total Mercury Measurement ($Hg^T$)

In the first analytical path, a connector 62 directs a sample stream through a thermal pyrolysis unit 64 ("thermal pyrolyzer"), which is heated within a pyrolyzer oven that defines a heated pyrolysis zone 66. Thermal pyrolyzer 64 is exposed directly to the gas sample, and is used to convert all mercury forms present in the sample into elemental form.

Exhaustive tests performed by the inventors revealed that conventional fill materials for thermal pyrolyzers, such as quartz chips, stainless steel, carbon, alumina, and molecular sieve materials, all produced excessive recombination after a period of continuous running, even when samples of stack gas were greatly reduced in concentration through prior dilution. In contrast, the inventors have realized that inert covalently bonded materials like silicon carbide (e.g. SiC), silicon oxides ($SiO_n$, n=1-2), silicon nitride (e.g. $Si_3N_4$), silicon boride (e.g. $SiB_6$), boron nitride (e.g. BN) or mixtures thereof, provide the unique ability to reduce all forms of mercury to elemental form, and further, to prevent recombination before removal of acid gas species. These materials are resilient as a material for thermal pyrolyzers, operating over a wide temperature range and processing samples of a wide variety of stack gas compositions.

In accordance with one embodiment of the invention, thermal pyrolyzer 64 contains one or more of the above-mentioned materials as a fill material 67. The material may be in coarse granular form, for example, to allow passage of the sample gas therethrough. In a variant embodiment, a long, narrow tube of at least one of the above-mentioned materials (e.g. a silicon carbide denuder) is employed in thermal pyrolyzer 64.

The term "SiC" includes all forms and phases of silicon carbide. In an embodiment of the invention, SiC is crystalline silicon carbide. In a further embodiment, the material for the thermal pyrolyzer used is standard industrial grade SiC, which is typically employed for a different purpose in other industrial applications, namely as an abrasive. However, this material may provide some practical advantages when used with thermal pyrolyzers in the context of this embodiment of the invention, in that the material is relatively inexpensive and readily available. A typical analysis of silicon carbide used in one example implementation is as follows:

SiC Typical Chemical Analysis
Silicon Carbide: 98.4%
Silicon: (Free) 0.63%
Silicon Dioxide: (Free) 0.57%
Carbon: (Free) 0.25%
Iron: 0.16%
Aluminum: 0.23%
Calcium Oxide: 0.05%
Magnesia: 0.05%

In a further embodiment of the invention, the material for the thermal pyrolyzer comprises silica ($SiO_2$), in one of its many crystalline or amorphous forms, either alone or in combination with one or more of the above-mentioned inert covalently bonded materials. When silica is present in the thermal pyrolyzer in combination with another inert covalently bonded material, it may be present as part of a primarily homogeneous mixture with that material or as a coating on the surface of particles comprising that material. This layer of silica may be formed by depositing the silica on the surface of the material using any well known deposition method (for example, vapor deposition or chemical deposition from a solution) prior to use of the material in a thermal pyrolyzer, or it may be formed on the surface of the particles by oxidation of the material under the reaction conditions for pyrolysis of the sample stream (e.g. by heating in an oxygen-containing environment). The layer of silica may be as little as 100 angstroms thick. Materials that undergo oxidation to form a layer of silica on the surface of said material, include, but are not limited to, SiC, SiO and other suitable Si-bearing materials such as, but not limited to, fused silica, quartz and silica sand. When silica is utilized as the bulk of the thermal pyrolyzer material on its own, in admixture with another pyrolyzer material or as a layer or coating on another pyrolyzer material, it is an embodiment of the invention that it is used in any of its well known crystalline forms, including cristobalite, quartz, tridymite, coesite, stishovite and mixtures thereof. In an embodiment of the invention, the silica is cristobalite. In a further embodiment of the invention, the thermal pyrolyzer comprises cristobalite silica either as the bulk of the pyrolyzer material or as a layer or coating on SiC or other suitable Si-bearing materials. Such other materials may include, but are not limited to, fused silica, quartz, and silica sand; in particular, silica sand (for example quartz sand).

In variant embodiments of the invention, other covalently bonded materials similar to the materials identified above may be employed in thermal pyrolyzer 64.

The gas sample in this analytical path is pulled through thermal pyrolyzer 64 to convert the sample into pyrolyzed gas, in which all mercury in the sample is reduced to elemental form. Since thermal pyrolyzer 64 is exposed directly to the gas sample (e.g. derived from the sample originally obtained from stack 20 of FIG. 1), the mercury (now converted into elemental form) in the pyrolyzed gas can be detected by a mercury analyzer (e.g. mercury analyzer 56 of FIG. 1) to measure the concentration of total mercury in the gas sample (i.e. accounting for both mercury that was originally in elemental form and mercury that was originally in ionic form).

In one embodiment of the invention, thermal pyrolyzer 64 comprises a tailpiece 68. Tailpiece 68 is described in greater detail with reference to FIG. 3.

Figure 3:
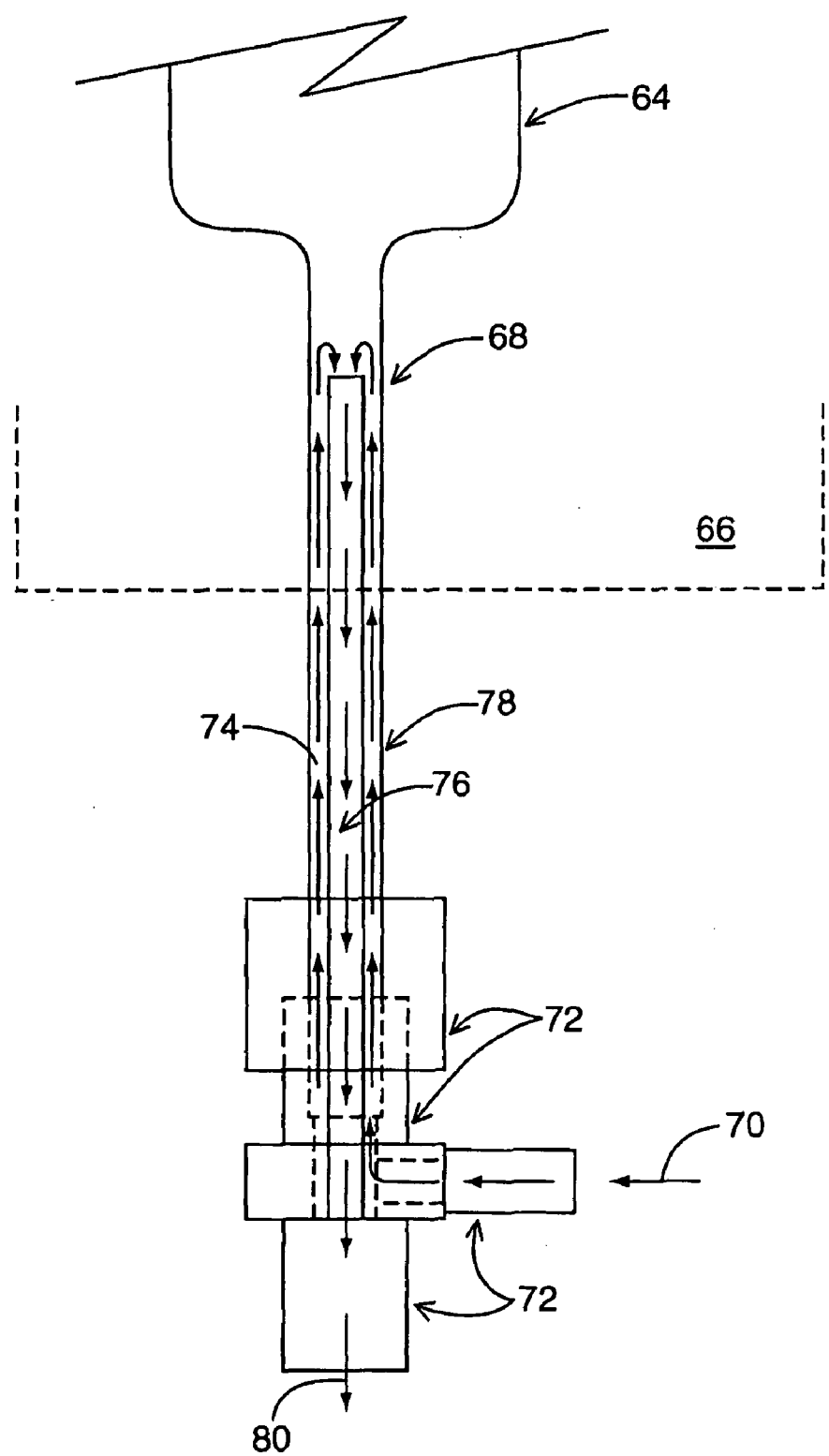
FIG. 3 is a schematic diagram of a tailpiece of a thermal pyrolysis unit for a conditioning module in an embodiment of the invention.

Referring to FIG. 3, a schematic diagram of a tailpiece of a thermal pyrolysis unit for a conditioning module in an embodiment of the invention is shown generally as 68.

The design of tailpiece 68 in this embodiment of the invention addresses a number of potential problems that may arise in the analysis of a gas sample. Any elemental mercury in the heated pyrolysis zone 66 will have a natural tendency to combine as it cools down after exiting the heated zone. The presence of free halogens (e.g. $Cl_2$) and oxidizing gases (e.g. HCl) can make recombination even more likely. Any ionic mercury compounds so produced would coat the surfaces of conditioning elements, which can result in slow response and carryover. Furthermore, where ionic mercury present at this point (whether originally present or newly created by recombination) is subsequently scrubbed from the sample stream, this may result in an anomalously low total mercury measurement. Moreover, trace compounds present in virtually all coal-fired power plant gas matrices will typically leave residual deposits at the exit of a thermal pyrolyzer. For example, ammonia salts may be created, where ammonia has been injected into the matrix as part of pollution abatement techniques. These volatile, water-soluble salts sublimate out when the sample gas cools after exiting the thermal pyrolyzer. These deposits can retain mercury and release it later, which can generate anomalous measurements. In severe cases, the deposits can build up and restrict the flow of gases through the conditioning module.

In accordance with this embodiment of the invention, the tailpiece 68 for a thermal pyrolyzer 64 facilitates the prompt and efficient removal of offending gases before recombination can occur, and the flushing of deposits before they can build up to create analytical problems. The design of tailpiece 68 is such that a scrubbing liquid (e.g. water, or other reagant) is introduced directly into the heated tail of thermal pyrolyzer 64. The scrubbing liquid enters at 70 through one connector of an arrangement of connectors and fittings 72 (e.g. made of Teflon), into an outer jacket 74 defined by an inner tube 76 and the inner surface of concentric outer tube 78 of tailpiece 68. The scrubbing liquid is carried upwards within outer jacket 74 directly into heated pyrolysis zone 66, so that the acid gas and deposit removal process occurs directly within heated pyrolysis zone 66.

In this embodiment of the invention, inner tube 76 is made of nickel or other inert material so as not to cause mercury losses. Outer tube 78 of tailpiece 68 is made of quartz glass, which has good thermal insulating properties. Accordingly, at the point where scrubbing liquid is introduced, tailpiece 68 and the sample gas is still sufficiently hot so that recombination cannot occur. This high gas temperature is possible due to the insulating characteristics of outer tube 78 of tailpiece 68.

This construction for tailpiece 68 also eliminates any "dry" areas where mercury could recombine and where resultant $HgCl_2$ could deposit, which can result in slow response times. The efficient flushing action produced by the scrubbing liquid ensures that any soluble acid gases in the sample stream are dissolved into the liquid, and are removed from the gaseous sample stream while the sample is emerging from thermal pyrolyzer 64 and is still hot, before recombination can occur. This flushing action also efficiently removes all water-soluble salts that might otherwise build up in tailpiece 68.

The sample gas and scrubbing liquid are carried out via inner tube 76, and out of tailpiece 68 at 80. The sample gas and scrubbing liquid can be separated in subsequent processing. The alternating bubbles of liquid and gas in the sample stream within tailpiece 68 of thermal pyrolyzer 64 provide sufficient surface area for acid gases to be dissolved into the liquid. As well, the action of the liquid ensures that all of the surfaces downstream of thermal pyrolyzer 64 are continuously washed, removing deposits that would otherwise build up over time.

Referring again to FIG. 2, in one embodiment of the invention, the pyrolyzed gas produced by thermal pyrolyzer 64 is subsequently scrubbed using a scrubber unit 82 before being passed to a mercury analyzer. Scrubber unit 82 removes water-soluble acid gases, such as hydrogen chloride, sulfur dioxide, sulfur trioxide, and oxides of nitrogen from the pyrolyzed gas, yielding a sample that may be more safely analyzed by the mercury analyzer. Scrubber unit 82 also removes moisture in the pyrolyzed gas to prevent condensation in downstream lines leading to the mercury analyzer. Scrubber unit 82 in this embodiment of the invention is described in greater detail with reference to FIG. 4.

Figure 4:
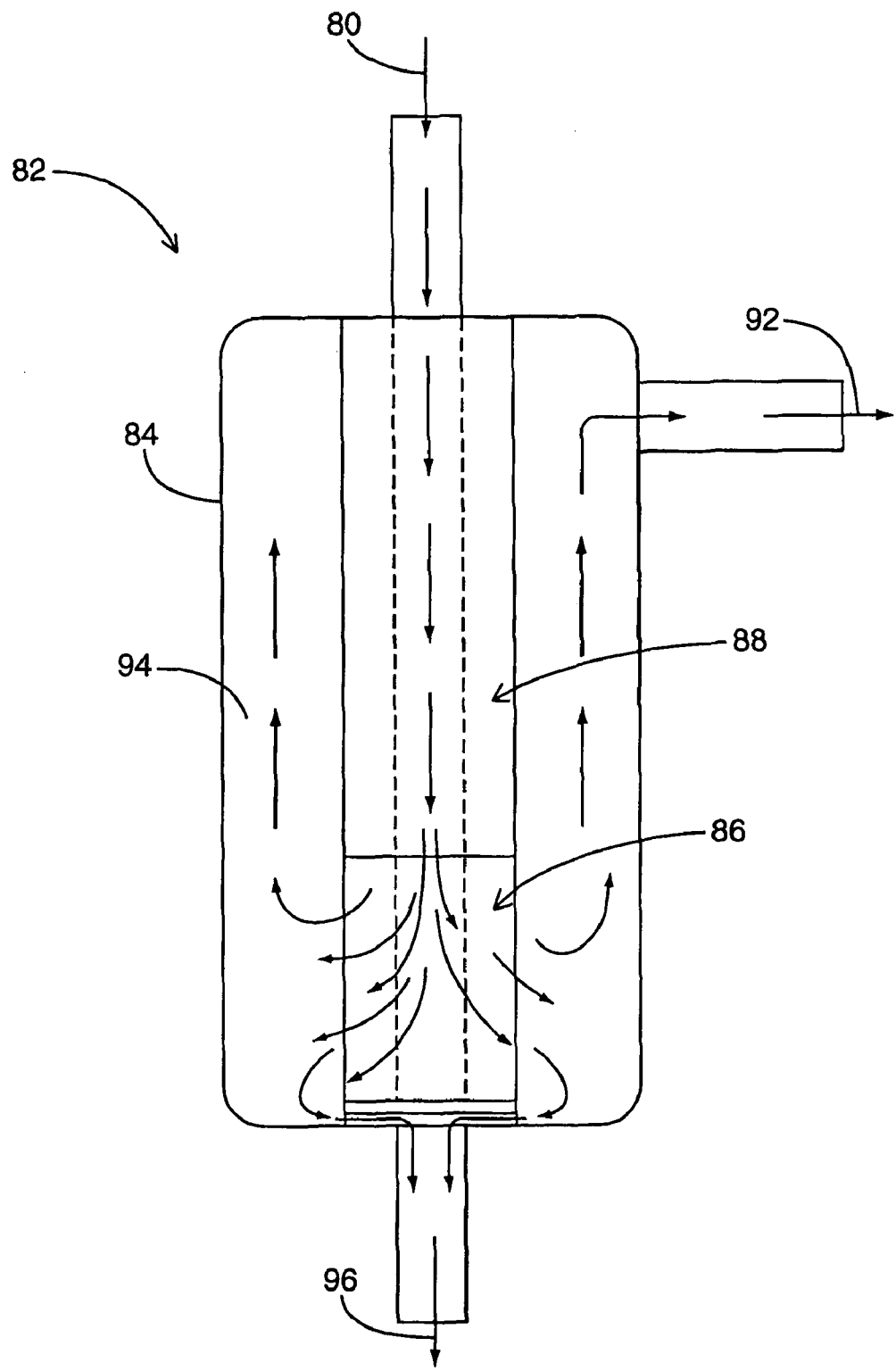
FIG. 4 is a schematic diagram of a scrubber unit for a conditioning module in an embodiment of the invention.

Referring to FIG. 4, a schematic diagram of a scrubber unit for a conditioning module in an embodiment of the invention is shown generally as 82. In this embodiment of the invention, scrubber unit 82 forms a part of the first analytical path (total mercury measurement) in conditioning module 34 of FIG. 2, and is connected directly after tailpiece 68 of thermal pyrolyzer 64. Scrubber unit 82 is used to separate the scrubbing liquid from the gaseous sample. Pyrolyzed gas is received as input to scrubber unit 82 at 80, and is forced to pass through a coalescing filter element.

In one implementation, scrubber unit 82 is a conventional commercially available disposable filter unit (DFU) 84 containing a coalescing filter element 86 extending from a solid body portion 88, and modified so that the filter element 86 is reduced in size and mounted within a lower, cooled region of scrubber unit 82. The entire scrubber unit 82 is chilled (e.g. to approximately 3° C. by a chiller block 90 in one example implementation, as shown in FIG. 2) so that the dew point of the resulting gas at 92 is lower than the ambient temperature of the mercury analyzer.

The liquid/gas mixture of the pyrolyzed gas is introduced through a center top fitting at 80 and runs into the filter element 86, which becomes saturated with the scrubbing liquid. Filter element 86 provides a medium for capturing a wide range of water-soluble species into the aqueous phase. Filter element 86 is also effective at scrubbing out sulphur trioxide aerosols that may be present, for example, which typically passes through conventional impingers without being trapped. The pyrolyzed gas passes through filter element 86, travels upwards through an outer annular area 94, and emerges through a side port fitting at 92, which may then be passed to a mercury analyzer for analysis. This unit provides intimate contact between the gas stream and the liquid scrubbing medium, allowing for efficient removal of residual acid gases.

The gas is chilled as it passes up the outer annular area 94, and moisture condenses on the inner and outer walls of the DFU 84. Both liquid previously added (e.g. as discussed with reference to FIG. 3) and the condensate formed during cooling will drain out of the DFU 84 through the bottom fitting at drain outlet 96 to drain 98 (FIG. 2), to ensure rapid removal of the liquid, and to prevent standing liquid from collecting in scrubber unit 82. If the chillers are operated at negative pressure, an active pumping system is required to remove the liquid in scrubber unit 82. If operated under positive pressure, only a flow restrictor is required to produce the draining action. The draining action permits scrubber unit 82 to have low internal dead volume and no reservoir of liquid, enabling it to respond rapidly to changes in sample concentration. If liquid were allowed to remain in the filter unit for extended periods, it would become acidic. This acidic liquid would foster oxidation of mercury. This oxidized mercury would then be removed along with the liquid, resulting in analytical losses within the system.

Although simple, inexpensive, and disposable, a DFU will typically last for several months of continuous operation in a typical coal-fired power plant installation.

Referring again to FIG. 2, pyrolyzed gas is scrubbed as it passes through the scrubber unit 82, and emerges at 92 as scrubbed gas, which may then be passed to a mercury analyzer (e.g. mercury analyzer 56 of FIG. 1) for analysis. It is desirable to maintain the flow rate through conditioning module 34 at a constant level. Flow through conditioning module 34 is provided by either a pump located within the mercury analyzer 56 or by a bypass pump and flow regulator 100, 102 to a vent 104, depending on the setting of valves 106, 108. These elements will be described in further detail later in this description following discussion of the second analytical path, provided below.

Second Analytical Path: Elemental Mercury Measurement ($Hg^0$)

In the second analytical path, connectors 62, 110 direct a sample stream to a separate scrubber unit 112 in an embodiment of the invention. Any excess sample gas not required for analysis may be vented through vent 148. In this embodiment, scrubber unit 112 samples directly from the sample stream and is used to remove water-soluble (i.e. ionic) forms of mercury from the sample prior to subsequent processing. Scrubber unit 112 is also used to remove harmful potential interferents from the sample in producing a scrubbed gas at 114. As a result, while ionic forms of mercury will be scrubbed out, the elemental mercury originally present in the sample will be quantitatively passed through scrubber unit 112 in producing scrubbed gas at 114. As a result, the mercury detected in scrubbed gas 114 can be used to obtain a measure of the concentration of elemental mercury originally present in the sample.

In one embodiment of the invention, scrubber unit 112 is of a different design than scrubber unit 82, to account for the fact that the sample stream to which scrubber unit 112 is exposed may contain significant concentrations of $HgCl_2$. Unlike scrubber unit 82, which is exposed only to elemental mercury in the first analytical path, scrubber unit 112 in the second analytical path is exposed to the full stack gas matrix, which can include both elemental mercury and $HgCl_2$. As a result, the surface area inside of a scrubber unit 112 must be minimized in order to reduce deposition of $HgCl_2$. Any ionic mercury compounds that form deposits would coat the surfaces of conditioning elements, which can result in slow response time and carryover.

Furthermore, as much of all exposed surfaces within a scrubber unit 112 should be wetted to remove any deposited mercury chloride. In the embodiment of the invention shown in FIG. 2, water is used as a scrubbing liquid, and supplied to the sample stream from a reservoir 116 by a peristaltic pump motor 118 through connector 110 (alternatively, a pressurized water supply may be used). Reservoir 116 also supplies water for the first analytical path via tailpiece 68 described earlier with reference to FIG. 3.

While a range of chemical reagents may be used in scrubber units 82 and 112, the ability of a conditioning module design that works with plain water can provide certain advantages over conventional approaches. For example, plain water is readily available, inexpensive, and does not require special preparation or disposal.

A scrubber unit 112 designed in accordance with an embodiment of the invention will now be described in greater detail with reference to FIG. 5.

Figure 5:
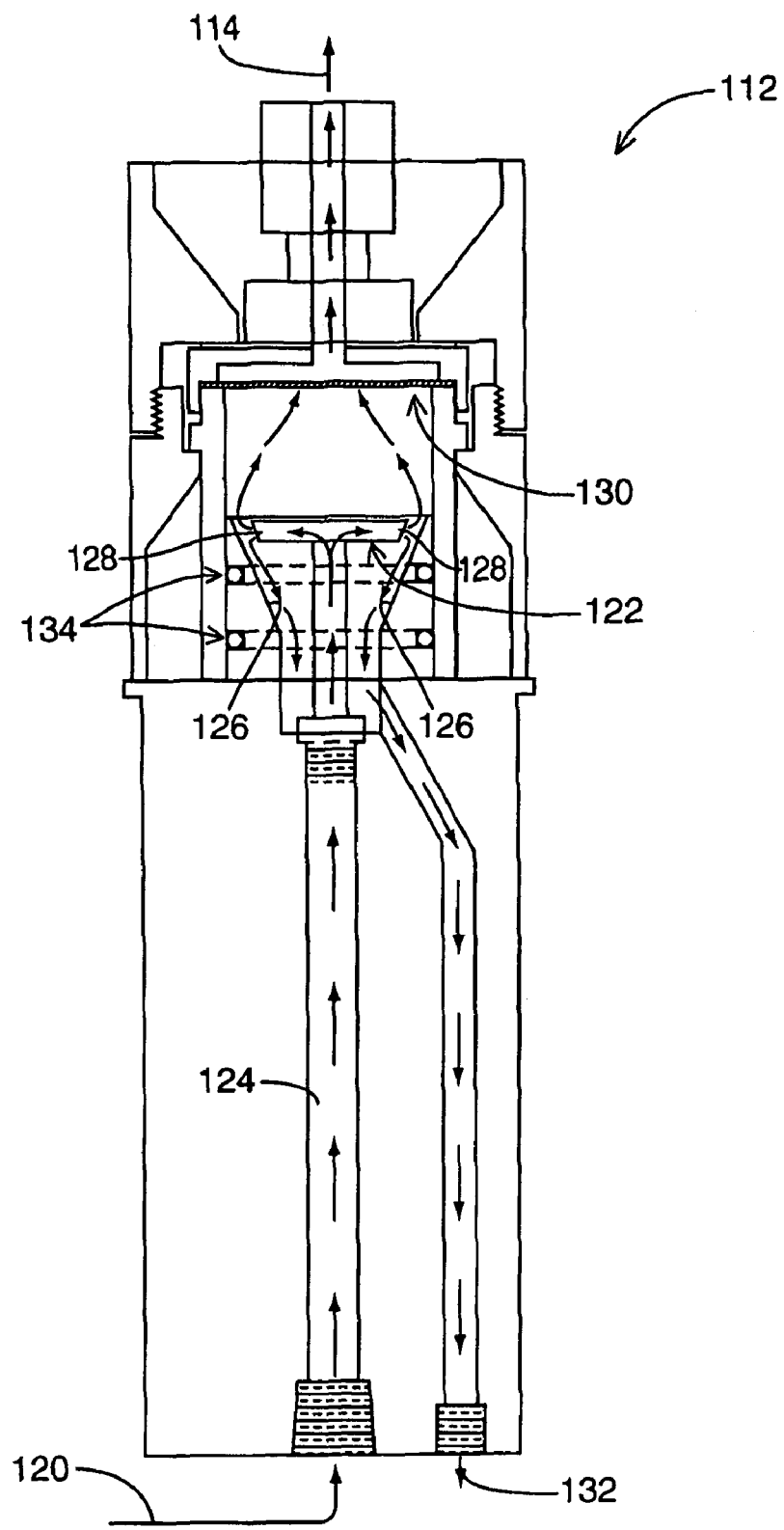
FIG. 5 is a schematic diagram of another scrubber unit for a conditioning module in an embodiment of the invention.

Referring to FIG. 5, a schematic diagram of a scrubber unit for a conditioning module in an embodiment of the invention is shown generally as 112. In this embodiment of the invention, scrubber unit 112 forms a part of the second analytical path (elemental mercury measurement) in conditioning module 34 of FIG. 2. Scrubber unit 112 is used to remove mercury chloride and other acid gas components while allowing elemental mercury in the sample stream to pass through unimpeded. Accordingly, scrubber unit 112 facilitates more accurate determination of the elemental mercury originally present in the initial sample. Scrubber unit 112 also acts as a liquid/gas separator to ensure that only dry sample gas is passed on, for output to a mercury analyzer, for example.

In this embodiment, scrubber unit 112 is made out of Teflon-coated metal, although other inert materials may also be used. Scrubbing liquid is introduced into the sample stream ahead of scrubber unit 112 via a conventional T-fitting of connector 110 (FIG. 2). The mixed liquid/gas sample enters through a bottom fitting at 120. A T-shaped distributor fitting 122 at the top of an entry tube 124 ejects liquid horizontally so that it coats the sides 126 of scrubber unit 112. Although distributor fitting 122 is shown with two nozzles 128 in FIG. 5, distributor fitting 122 may have a different number of nozzles 128 in variant implementations.

Sample gas proceeds upwards and passes through a hydrophobic (e.g. Teflon) filter membrane 130 and exits at 114. Only gas can pass through this filter membrane 130. The liquid ejected through distributor fitting 122 is ejected sideways so that liquid droplets do not come into contact with filter element 130. This prevents plugging and fouling of the filter element that might otherwise occur as impurities in the liquid stream evaporate after being deposited on filter membrane 130.

The liquid ejected from distributor fitting 122 runs downward and coats the sides 126 of scrubber unit 112. This results in an efficient washing of the inner surfaces of scrubber unit 112. This washing action is performed to remove all traces of gaseous $HgCl_2$ and other soluble salts. The liquid is removed via a drain outlet at 132 to drain 98 (FIG. 2). The low internal volume and minimal exposed surface area ensure quick removal of all liquids and rapid exchange of gases. This minimizes buildup of residual mercury chloride and its subsequent release into the analytical gas stream.

For convenience, the entire top of scrubber unit 112 may be removable to allow easy changing of filter membrane 130, in a variant embodiment of the invention. The top can be pushed on and held in place by dual O-rings 134.

It will be understood by persons skilled in the art that additional pyrolyzer units or scrubber units may optionally be employed in either or both of the first and second analytical paths for added safety in variant implementations, and such variant implementations are intended to be within the scope of the invention.

Sample Switching Unit

Referring again to FIG. 2, sample gas processed by conditioning module 34 is split into two separate analytical paths, with the gas being passed through each of the two paths continuously. This allows both a total mercury measurement and an elemental mercury measurement to be obtained. In one example implementation, separate mercury analyzers may be employed so that both of these measurements can be made simultaneously. In this case, a first mercury analyzer is used to analyze gas emerging as output from the first path, while a second mercury analyzer is used to analyze gas emerging as output from the second path.

In another example implementation, as shown in FIG. 2, a switching unit is implemented using two four-way inert solenoid valves 106, 108. Valves 106, 108 are actuated to direct gas from one path to a mercury analyzer (e.g. via output 152 to a mercury analyzer 56 of FIG. 1). If desired, the switching unit can be employed to enable a single mercury analyzer to alternately sample gases emerging as output from the first and second paths respectively.

In another example implementation, multiple conditioning modules may be cascaded to allow multiple stacks to be monitored using a single mercury analyzer. In this case, input 150 can accept the output 152 from a previous cascaded conditioning module 34 and present it to the mercury analyzer 56.

If the conditioning module 34 is "not ready" for any reason, zero air (e.g. via input 150 when conditioning module 34 is not coupled to another conditioning module) can be directed to the mercury analyzer to prevent contamination of, or damage to the analyzer. Valves 106, 108 are also coupled to a vent at 104 via bypass pump and flow regulator 100, 102. This permits all idle paths within the switching unit to be continually flushed. If the analyzer is not sampling a particular sampling path, bypass pump and flow regulator 100, 102 ensure that sample gas continues to flow through the paths of conditioning module 34 at approximately the same flow rate to ensure that components along the path remain conditioned and in equilibrium.

As indicated earlier, gas emerging as output from the first path may be used to obtain a total mercury measure ($Hg^T$), while gas emerging as output from the second path may be used to obtain an elemental mercury measure ($Hg^0$) by the mercury analyzer. These two measures can also be used to determine a third measure: an ionic mercury measure calculated as the difference between the total and elemental mercury measures.

Additional Considerations

While not explicitly shown in FIG. 2, it will be understood by persons skilled in the art that conditioning module 34 will generally comprise other elements, such as heating elements, temperature sensors, pressure sensors, back-up protection sensors, control switches, and fan elements, for example, for use in the operation and control of conditioning module 34. Probe temperatures, flow rates and pressures within conditioning module 34, for example, can be monitored and telemetered to the system controller via a data communications link [not shown].

It will also be understood by persons skilled in the art, that the above description of conditioning module 34 relates to a number of example implementations, and that other types and constructions of conditioning module 34 may be employed in variant implementations of CEM 10 without departing from the scope of the invention.

For example, although the example implementation of FIG. 2 employs a conditioning module 34 that speciates mercury, a subset implementation used only for total mercury measurement may be constructed. One such implementation may comprise a single pyrolyzer unit, and a single chiller component with no switching valves, for example.

By way of further examples, the use of such inert covalently bonded materials such as silicon carbide (SiC), silicon oxides ($SiO_n$, n=1-2), silicon nitride (e.g. $Si_3N_4$), silicon boride (e.g. $SiB_6$), boron nitride (e.g. BN) or mixtures thereof can be employed in thermal pyrolyzers within conditioning modules and systems where speciation is not attempted. The coalescing filter and hydrophobic filter element described herein can be used to remove acid gases from sample streams, pyrolyzed or not pyrolyzed, in conditioning modules and systems where speciation is not attempted. Such variants are intended to be within the scope of the invention.

Figure 6:
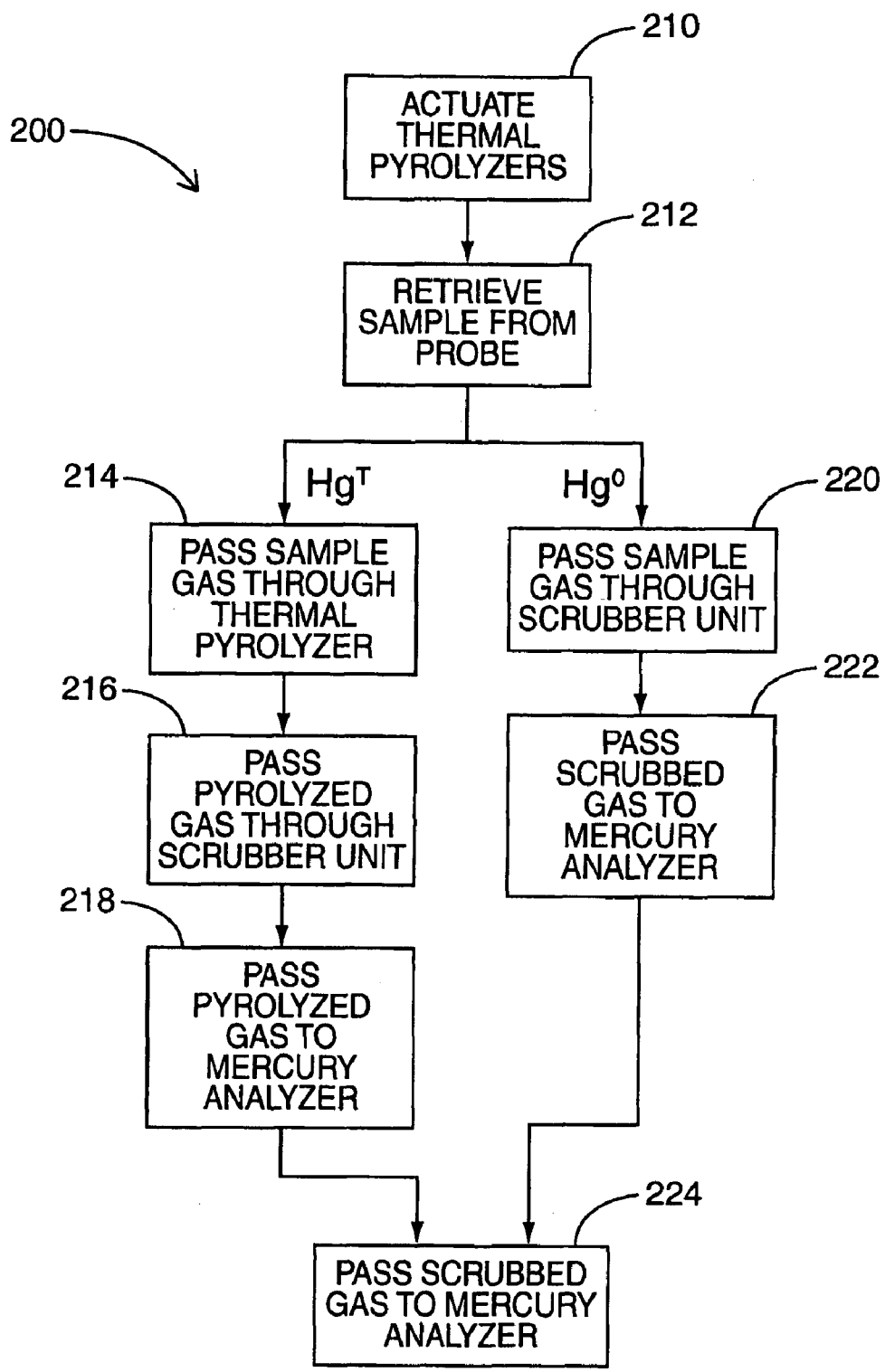
FIG. 6 is a flowchart illustrating steps of a method for measuring mercury in gaseous emissions in an embodiment of the invention.

Now referring to FIG. 6, a flowchart illustrating steps of a method for measuring mercury in gaseous emissions in an embodiment of the invention is shown generally as 200. The details of certain steps of method 200 are provided in summary form; additional details with respect to various steps of method 200 can be found in the above description.

At step 210, in preparation for the conditioning process, thermal pyrolyzers of a conditioning module (e.g. thermal pyrolyzer 64 of conditioning module 34 in FIG. 2) are heated before gases to be analyzed are passed therethrough. The scrubbers are cooled to their required temperature. Thereafter, the conditioning components are continually maintained at their optimum temperatures.

In this embodiment, the conditioning process is a continuous process, and the following steps are performed continuously.

At step 212, a sample of mercury-containing stack gases is retrieved from a sampling probe (e.g. sampling probe 32 of FIG. 1). In one example implementation, the sample is diluted at the sampling probe.

The sample gas is the split into two streams, and fed continuously and simultaneously to two different analytical paths. Unneeded gas is vented.

First Analytical Path

Within the first analytical path, at step 214, the sample gas is passed through a thermal pyrolyzer to reduce the mercury therein to elemental form, producing a pyrolyzed gas. In accordance with an embodiment of the invention, the thermal pyrolyzer contains an inert covalently bonded material selected from silicon carbide (SiC), silicon oxides ($SiO_n$, n=1-2), silicon nitride (e.g. $Si_3N_4$), silicon boride (e.g. $SiB_6$), boron nitride (e.g. BN) and mixtures thereof as fill material. In accordance with an embodiment of the invention, the thermal pyrolyzer comprises a tailpiece described with reference to FIG. 3. At step 216, the pyrolyzed gas is then passed through a scrubber unit (e.g. scrubber unit 82 of FIG. 2). In accordance with an embodiment of the invention, the scrubber unit contains a coalescing filter element as described with reference to FIG. 4. Output from the scrubber unit can then be passed to a mercury analyzer (e.g. mercury analyzer 56 of FIG. 1) at step 218, to determine a total mercury measure from the elemental mercury in the pyrolyzed gas.

Second Analytical Path

Within the second analytical path, at step 220, the sample gas is passed through a scrubber unit (e.g. scrubber unit 112 of FIG. 2) to remove substantially all water-soluble forms of mercury therefrom and quantitatively pass elemental mercury. In accordance with an embodiment of the invention, this scrubber unit contains a hydrophobic filter membrane as described with reference to FIG. 5. Scrubbed gas produced by the scrubber unit can then be passed to a mercury analyzer at step 222, to determine an elemental mercury measure from the scrubbed gas.

Path Selection

In one implementation where the use of a single mercury analyzer is desired, valves and switches may be employed to allow selection of one of the two paths for analysis at a particular point in time, as indicated at step 224. In another implementation, the gas from both analytical paths can be sent to separate mercury analyzers for analysis [step 224 is not performed]. The mercury analyzer(s) used in determining the total and elemental mercury measures can also be used to determine an ionic mercury measure, by calculating the difference between the total and elemental mercury measures.

As indicated earlier with respect to conditioning module 34, variations may be made to the method 200 without departing from the scope of the invention. For example, in a variant embodiment, a method may comprise steps to process a sample gas using only one analytical path, to determine a total mercury measurement.

While embodiments of the invention have been described herein with reference to a system in which a diluted sample is processed, in variant implementations, embodiments of the invention may also be employed in systems in which the samples to be processed are not diluted.

The invention has been described with reference to particular implementations and embodiments. However, it will be understood by persons skilled in the art that a number of other variations and modifications are possible without departing from the scope of the invention.

The invention claimed is:

1. A process for pyrolyzing ionic mercury into gaseous elemental form comprising the steps of:
   a) receiving mercury-containing gas to be passed through a thermal pyrolysis unit, wherein the thermal pyrolysis unit contains pyrolyzer material comprising an inert covalently bonded material selected from silicon carbide (SiC), silicon nitride (e.g. $Si_3N_4$), silicon boride (e.g. $SiB_6$), boron nitride (e.g. BN) and mixtures thereof; and b) converting any ionic mercury-containing gas into pyrolyzed gas containing elemental mercury, by passing the mercury-containing gas through the pyrolyzer material.

2. The process according to claim 1, wherein the pyrolyzer material is SiC.

3. The process according to claim 1 including providing a layer of silica on the surface of particles comprising an inert covalently bonded material selected from silicon carbide (SiC), silicon oxides ($SiO_n$, n=1-2), silicon nitride (e.g. $Si_3N_4$), silicon boride (e.g. $SiB_6$), boron nitride (e.g. BN) and mixtures thereof.

4. The process according to claim 3, wherein the layer of silica is formed on the surface of the inert covalently bonded material during pyrolysis.

5. The process according to claim 3, wherein the layer of silica is formed on the surface of the inert covalently bonded material by deposition prior to use of the material as a thermal pyrolyzer.

6. The process according to claim 3, wherein the inert covalently bonded material is SiC, SiO, fused silica, quartz or silica sand.

7. The process according to claim 6, wherein the inert covalently bonded material is SiC or silica sand.

8. The process of claim 1, including providing mercury-containing gas from a sample of stack gas, for use in determining mercury levels in the stack gas.

9. A process for pyrolyzing ionic mercury into gaseous elemental form comprising the steps of:
   (a) receiving mercury-containing gas to be passed through a thermal pyrolysis unit, wherein the thermal pyrolysis unit contains pyrolyzer material comprising an inert covalently bonded material selected from silicon carbide (SiC), silicon oxides ($SiO_n$, n=1-2), silicon nitride (e.g. $Si_3N_4$), silicon boride (e.g. $SiB_6$), boron nitride (e.g. BN, and mixtures thereof,
   (b) converting any ionic mercury-containing gas into pyrolyzed gas containing elemental mercury, by passing the mercury-containing gas through the pyrolyzer material, and
   (c) heating the thermal pyrolysis unit with a heated pyrolysis zone, wherein the process further comprising the step of injecting a scrubbing liquid into the pyrolyzed gas such that the scrubbing liquid is introduced to the pyrolyzed gas within the heated pyrolysis zone, and causing the scrubbing liquid to contact the pyrolyzed gas to remove oxidizing gases that tend to promote recombination at the elemental mercury to form ionic mercury compounds, before the pyrolyzed gas cools and recombination occurs.

10. The process of claim 9, wherein the scrubbing liquid is water.

11. A process for pyrolyzing ionic mercury into gaseous elemental form comprising the steps of:
   (a) receiving mercury-containing gas to be passed through a thermal pyrolysis unit, wherein the thermal pyrolysis unit contains pyrolyzer material comprising an inert covalently bonded material selected from silicon carbide (siC), silicon oxides ($SiO_n$, n=1-2 silicon nitride (e.g. $Si_3N_4$), silicon boride (e.g. $SiB_6$), boron nitride (e.g. BN) and mixtures thereof,
   (b) converting any ionic mercury-containing gas into pyrolyzed gas containing elemental mercury, by passing the mercury-containing gas through the pyrolyzer material, and
   (c) heating the thermal pyrolysis unit with a heated pyrolysis zone, wherein the process further comprising the steps of: providing a coalescing filter element, said coalescing filter element comprising a membrane; wetting the membrane; and passing the pyrolyzed gas through the membrane.

12. A thermal pyrolysis unit for pyrolyzing ionic mercury in mercury-containing gas passed therethrough into gaseous elemental form to produce a pyrolyzed gas, wherein the thermal pyrolysis unit contains pyrolyzer material comprising an inert covalently bonded material selected from silicon carbide (SiC), silicon nitride (e.g. $Si_3N_4$), silicon boride (e.g. $SiB_6$), boron nitride (e.g. BN) and mixtures thereof.

13. A process for pyrolyzing ionic mercury into gaseous elemental form comprising the steps of:
   (a) receiving mercury-containing gas to be passed through a thermal pyrolysis unit, wherein the thermal pyrolysis unit contains pyrolyzer material comprising an inert covalently bonded material selected from silicon carbide (SiC), silicon oxides ($SiO_n$, n=1-2 silicon nitride (e.g. $Si_3N_4$ silicon boride (e.g. $SiB_6$), boron nitride (e.g. BN) and mixtures thereof,
   (b) converting any ionic mercury-containing gas into pyrolyzed gas containing elemental mercury, by passing the mercury-containing gas through the pyrolyzer material, and
   (c) heating the thermal pyrolysis unit with a heated pyrolysis zone, wherein the process further comprising:
   taking a sample of stack gas from a stack;
   passing the stack gas sample through a filter;
   extracting one portion of the stack gas sample from the filter and returning a remaining portion of the stack gas sample to the stack; and
   diluting said one portion of the stack gas to form said mercury containing-gas.

14. The process of claim 13, including subjecting a first part of the mercury containing gas to steps (a) and (b), to enable the total mercury content of the stack gas to be determined, and subjecting a second part of the mercury containing gas to a process including scrubbing to remove ionic mercury, to enable the elemental mercury content to be determined.

* * * * *